United States Patent
Dowaki et al.

(10) Patent No.: US 8,994,940 B2
(45) Date of Patent: Mar. 31, 2015

(54) FINE PARTICLE MEASUREMENT APPARATUS AND OPTICAL AXIS CALIBRATION METHOD

(75) Inventors: Suguru Dowaki, Kanagawa (JP);
Shingo Imanishi, Kanagawa (JP);
Gakuji Hashimoto, Kanagawa (JP);
Shunpei Suzuki, Shizuoka (JP)

(73) Assignee: Sony Corporation, Tokyo (JP)

( * ) Notice: Subject to any disclaimer, the term of this patent is extended or adjusted under 35 U.S.C. 154(b) by 471 days.

(21) Appl. No.: 13/204,206

(22) Filed: Aug. 5, 2011

(65) Prior Publication Data

US 2012/0050737 A1 Mar. 1, 2012

(30) Foreign Application Priority Data

Aug. 24, 2010 (JP) ................................. 2010-186961

(51) Int. Cl.
| | |
|---|---|
| *G01N 15/02* | (2006.01) |
| *G01N 21/00* | (2006.01) |
| *G01N 21/47* | (2006.01) |
| *G01N 21/53* | (2006.01) |

(52) U.S. Cl.
CPC ............ *G01N 21/4785* (2013.01); *G01N 21/53* (2013.01); *G01N 2021/4707* (2013.01)
USPC ......... 356/338; 356/336; 356/343; 356/243.2

(58) Field of Classification Search
USPC .................................................. 356/335–343
See application file for complete search history.

(56) References Cited

U.S. PATENT DOCUMENTS

| | | | | |
|---|---|---|---|---|
| 5,646,597 A | * | 7/1997 | Hamburger et al. | 340/627 |
| 5,737,078 A | * | 4/1998 | Takarada et al. | 356/338 |
| 5,831,730 A | * | 11/1998 | Traina et al. | 356/336 |
| 2002/0057432 A1 | * | 5/2002 | Ortyn et al. | 356/338 |
| 2002/0135770 A1 | * | 9/2002 | Lewis et al. | 356/419 |
| 2003/0030811 A1 | * | 2/2003 | Lessure et al. | 356/437 |
| 2008/0024758 A1 | * | 1/2008 | Tabata | 356/39 |
| 2008/0316898 A1 | | 12/2008 | Itoh | |
| 2009/0122662 A1 | * | 5/2009 | Hosoda et al. | 369/44.23 |

(Continued)

FOREIGN PATENT DOCUMENTS

| | | |
|---|---|---|
| CN | 1906678 | 1/2007 |
| CN | 101403739 | 4/2009 |
| JP | 9-196916 | 7/1997 |

(Continued)

OTHER PUBLICATIONS

Chinese Office Action issued Aug. 19, 2014 in corresponding Chinese Application No. 201110236910.6.

*Primary Examiner* — Hoa Pham
*Assistant Examiner* — Sunghee Y Gray
(74) *Attorney, Agent, or Firm* — K&L Gates LLP

(57) ABSTRACT

Disclosed is a fine particle measurement apparatus including a light condensing unit that condenses irradiated light irradiated to a sample flow where fine particles pass through and directly propagates the light without scattering, and scattered light scattered by the fine particles to an optical receiver divided into a plurality of regions; a position controller that controls the relative positions of members of an optical path; and a control unit that detects positions of condensing spots of the irradiated light and the scattered light based on signal intensities of each region of the optical receiver, and controls the position controller such that the positions of the condensing spots of the irradiated light and the scattered light match with each other.

2 Claims, 9 Drawing Sheets

(56) References Cited

U.S. PATENT DOCUMENTS

2010/0231909 A1* 9/2010 Trainer .................. 356/336
2010/0315639 A1* 12/2010 Muraki .................. 356/342

FOREIGN PATENT DOCUMENTS

| JP | 11-83724 | 3/1999 |
| JP | 2007-46947 | 2/2007 |

* cited by examiner

FINE PARTICLE MEASUREMENT APPARATUS AND OPTICAL AXIS CALIBRATION METHOD

CROSS REFERENCES TO RELATED APPLICATIONS

The present application claims priority to Japanese Priority Patent Application JP 2010-186961 filed in the Japan Patent Office on Aug. 24, 2010, the entire contents of which are hereby incorporated by reference.

BACKGROUND

The present application relates to a fine particle measurement apparatus and an optical axis calibration method. More particularly, the disclosure relates to a fine particle measurement apparatus capable of automatically adjusting a positional relationship between a sample flow, where fine particles pass through, and a condensing spot of the light irradiated to the sample flow.

In the related art, a fine particle measurement apparatus is widely used, in which light (laser) is irradiated to an inner side of a flow cell or fine particles flowing through a flow path formed on a microchip, dispersed light from fine particles, fluorescent light generated from the fine particles or fluorescent substances labeled onto the fine particles is detected to measure optical properties of the fine particles. In such a fine particle measurement apparatus, a population (group) satisfying a predetermined condition as a result of the measurement of optical properties is often separately retrieved from the fine particles. In such an apparatus, a device capable of measuring the optical properties of, particularly, cells as the fine particles, or separately retrieving a cell group satisfying a predetermined condition is called a flow cytometer or a cell sorter.

For example, Japanese Unexamined Patent Application Publication No. 2007-46947 discloses "a flow cytometer having a plurality of light sources for irradiating a plurality of excitation light beams having different wavelengths in a predetermined cycle with different phases and an optical guide member for guiding a plurality of excitation light beams into the same incident optical path to condense them onto a dyed particle." The flow cytometer includes a plurality of light sources for irradiating a plurality of excitation light beams having different wavelengths, an optical guide member for guiding a plurality of the excitation light beams into the same incident optical path to condense them onto a dyed particle, and a plurality of fluorescence detectors for detecting fluorescent light generated from the particles excited by each of excitation light beams to output fluorescent signals (refer to Claims 1 and 3 and FIGS. 1 and 3 of Japanese Unexamined Patent Application Publication No. 2007-46947).

In the fine particle measurement apparatus of the related art, as shown in FIG. 8, the laser L is condensed from a direction approximately perpendicular to the sample flow S using the condensing lens 103. The fine particles P pass through the sample flow S to cross the spot of the condensed laser L. In this case, the intensity distribution of the laser spot has become a Gaussian distribution in which the intensity distribution is strong in the center of the spot and significantly decays at the periphery. FIG. 9 illustrates an exemplary intensity distribution of the laser spot in the fine particle measurement apparatus of the related art. For this reason, when the flow-sending position of the fine particles P within the sample flow S matches with the center position of the laser spot, the effective intensity of the laser irradiated to the fine particles P is maximized, and the obtained signal intensity is also maximized.

The operation of matching the flow-sending position of fine particle within the sample flow with the center position of the laser spot is generally called an "optical axis calibration." The optical axis calibration is carried out by flowing calibration micro beads and calibrating the position or focus of the condensing lens or centering the light source while histogram data is referenced to optimize the relative positions of the laser, the sample flow, the detector, and the like. Japanese Unexamined Patent Application Publication Nos. 11-83724 and 9-196916 also disclose calibration micro beads used in the optical axis calibration.

SUMMARY

The optical axis calibration for matching the positions of the sample flow and the laser spot with each other is important to carry out precise measurement by maximizing the signal intensity. However, in the related art, even when the optical axis calibration is carried out in advance, an apparatus may be vibrated during measurement, a pressure of the sheath flow or a temperature of the inner side of the apparatus may change, and the positions of the sample flow or the laser spot may change, so that the calibrated optical axis may be deviated. The optical axis deviation caused by vibration during measurement or changes in the pressure, the temperature, and the like may reduce the measurement precision, and in some cases, may make the measurement difficult.

In this regard, it is desirable to provide a fine particle measurement apparatus capable of automatically correcting the optical axis deviation and carrying out high precision measurement.

According to an embodiment, there is provided a fine particle measurement apparatus including: a light condensing unit that condenses irradiated light irradiated to a sample flow where fine particles pass through and directly propagates the light without scattering, and scattered light scattered by the fine particles to an optical receiver divided into a plurality of regions; a position controller that controls relative positions of members of an optical path; and a control unit that detects positions of condensing spots of the irradiated light and the scattered light based on signal intensities of each region of the optical receiver, and controls the position controller such that the positions of the condensing spots of the irradiated light and the scattered light match with each other.

In this fine particle measurement apparatus, by carrying out the optical axis calibration such that the positions of the irradiated-light condensing spot and the scattered-light condensing spot on the light-receiving surface of the optical receiver as the image points of the irradiated light and the scattered light match with each other, it is possible to match the position of the laser spot on the sample flow as an object point of the irradiated light with the position of the fine particle within the sample flow as an object point of the scattered light.

In this fine particle measurement apparatus, it is preferable that the light condensing unit include an optical filter having a blocking area for blocking the irradiated light and a transmitting area arranged around the blocking area to transmit the scattered light, the optical filter being disposed on an optical path between the sample flow and the optical receiver and arranged to be evacuated therefrom.

In addition, it is preferable that the optical receiver be equally divided into a plurality of regions by boundary lines intersecting at a single point on a light-receiving surface where the irradiated light and the scattered light are condensed to form a spot.

In this fine particle measurement apparatus, it is preferable that the light condensing unit further include an optical filter that splits a part of the scattered light based on a difference in the polarization direction on an optical path between the sample flow and the optical receiver, and wherein an optical filter that rotates the polarization direction of the irradiated light is disposed on an optical path between the optical filter and the sample flow or arranged to be evacuated therefrom.

According to another embodiment, there is provided an optical axis calibration method in a fine particle measurement apparatus, the including: condensing irradiated light irradiated to a sample flow where fine particles pass through and directly propagating the light without scattering, and scattered light scattered by the fine particles to an optical receiver divided into a plurality of regions; detecting positions of condensing spots of the irradiated light and the scattered light based on signal intensities of each region of the optical receiver; and calibrating the relative positions of members of an optical path such that the positions of the condensing spots of the irradiated light and the scattered light match with each other.

In the present disclosure, the "fine particles" widely includes biomedical fine particles such as cells, microbes, liposomes, or synthetic particles such as latex particles, gel particles, industrial particles.

The biomedical fine particles include chromosome, liposome, mitochondria, organelle, and the like included in various cells. The cells as a measurement target include animal cells (such as blood cells) and plant cells. The microbes include bacteriomycota such as a colon bacillus, viruses such as tobacco mosaic virus, bacteria such as yeast bacteria, and the like. In addition, the biomedical fine particle may include biopolymer such as nucleic acid or protein, or a complex thereof. The industrial particles may include, for example, organic or inorganic polymer materials, metals, and the like. The organic polymer material includes polystyrene, styrene/divinylbenzene, polymethylmethacrylate, and the like. The inorganic polymer material includes glass, silica, magnetic materials, and the like. Metal includes gold colloids, aluminum, and the like. While the fine particles typically have a spherical shape, they may have a non-spherical shape, and their size or mass is not particularly limited.

According to the present application, there is provided a fine particle measurement apparatus capable of automatically correcting a deviation of the optical axis and carrying out measurement with high precision.

Additional features and advantages are described herein, and will be apparent from the following Detailed Description and the figures.

DETAILED DESCRIPTION

Embodiments of the present application will be described below in detail with reference to the drawings.

The embodiments described below are intended only to illustrate an exemplary representative embodiment of the disclosure, and are not intended to limit the scope of the disclosure. Description will be made in the following sequence.

1. Fine Particle Measurement Apparatus According to First Embodiment

2. Fine Particle Measurement Apparatus According to Second Embodiment

Figure 1:
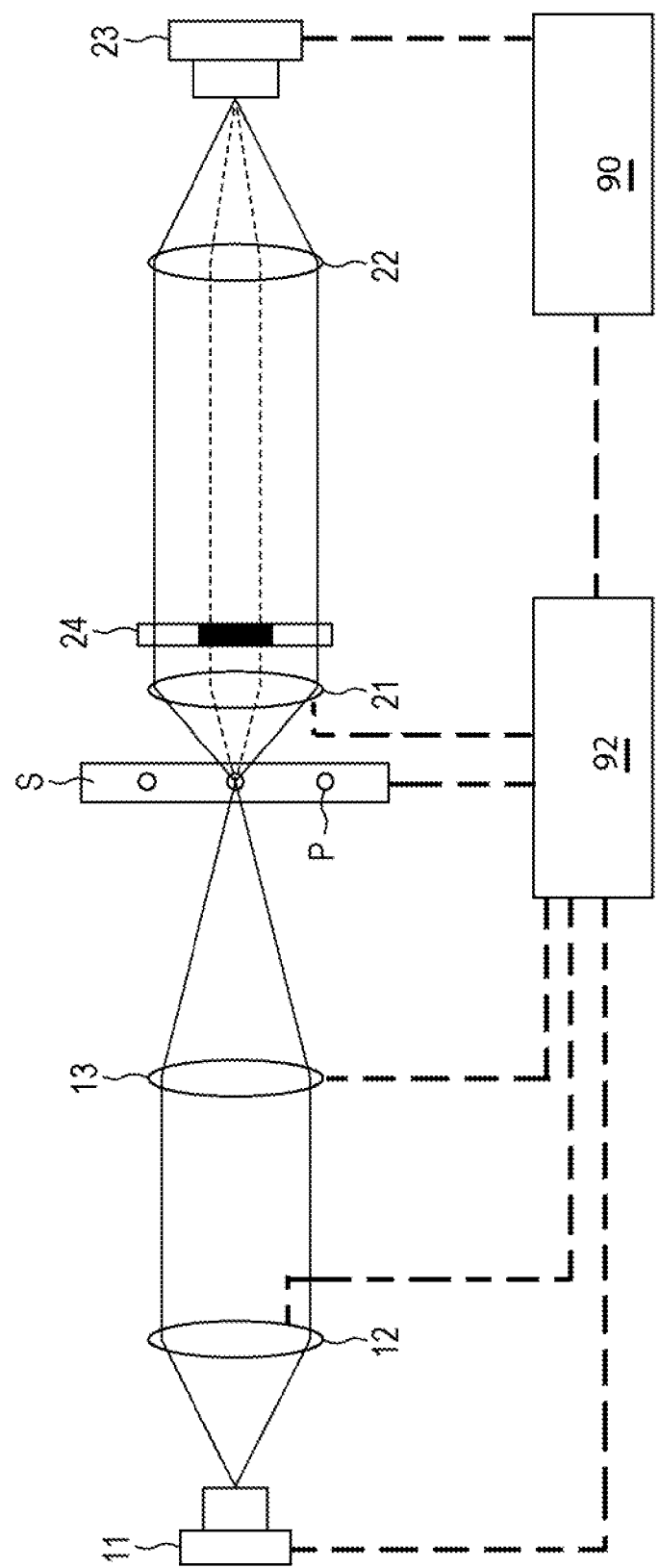
FIG. 1 is a schematic diagram illustrating a configuration of the optical path for detecting a position of the scattered-light condensing spot in a fine particle measurement apparatus according to a first embodiment of the disclosure.
Figure 2:
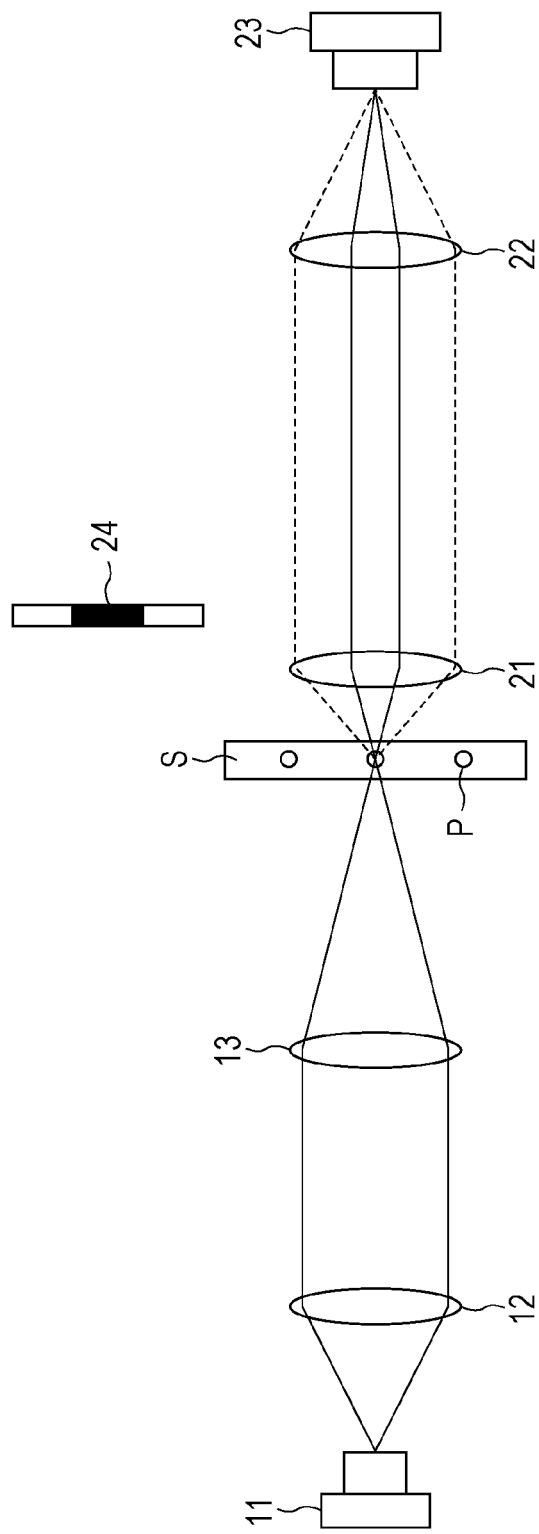
FIG. 2 is a schematic diagram illustrating a configuration of the optical path for detecting a position of the irradiated-light condensing spot in a fine particle measurement apparatus according to a first embodiment of the disclosure.

1. Fine Particle Measurement Apparatus According to First Embodiment (1) Light Condensing Unit FIGS. 1 and 2 are schematic diagrams illustrating a configuration of the optical path of the fine particle measurement apparatus according to a first embodiment of the disclosure. FIG. 1 illustrates a configuration of the optical path to detect a position of the condensing spot of the scattered light, and FIG. 2 illustrates a configuration of an optical path to detect a position of the condensing spot of the irradiated light.

In the drawings, the irradiated light (laser) emitted from the light source denoted by the reference numeral 11 is coupled to the substantially parallel light using the collimator lens 12 and condensed to the sample flow S, where the fine particles P pass through, using the condensing lens 13. The sample flow S may be sent within the flow path formed on the microchip or within the flow cell.

The irradiated light irradiated to the sample flow S and directly propagated without scattering, and the scattered light scattered by the fine particles P are coupled to the substantially parallel light using the object lens 21 and condensed using the condensing lens 22 to the optical receiver 23 divided into a plurality of areas (hereinafter, referred to as a "divided optical receiver 23"). The irradiated light and the scattered light condensed to the divided optical receiver 23 form a condensing spot on the light-receiving surface thereof.

In such an optical system, the irradiated light uses the laser spot on the sample flow S as an object point and uses the condensing spot on the light-receiving surface of the optical receiver 23 as an image point. In addition, since the scattered light is generated from the fine particles P, the object point corresponds to the fine particles P within the sample flow S, and the image point corresponds to the condensing spot on the light-receiving surface of the divided optical receiver 23.

In the drawings, the reference numeral 24 denotes an optical filter (hereinafter, referred to as a "mask 24") having a blocking area for blocking the irradiated light and a transmitting area for transmitting the scattered light disposed around the blocking area. The mask 24 can be interposed on the optical path between the sample flow S and the divided optical receiver 23 or arranged to be evacuated.

As shown in FIG. 1, when the mask 24 is interposed on the optical path between the sample flow S and the divided optical receiver 23, the irradiated light (represented by a dotted line in the drawings) directly propagating to the fine particles P without scattering is blocked by the blocking area disposed in the center of the mask 24. Therefore, only the scattered light scattered by the fine particles P is condensed to the divided optical receiver 23 using the condensing lens 22. In this case, the condensing spot of the scattered light condensed to the light-receiving surface of the divided optical receiver 23 is denoted by the reference symbol A in FIG. 3.

Meanwhile, as shown in FIG. 2, when the mask 24 is evacuated from the optical path between the sample flow S and the divided optical receiver 23, the irradiated light (represented by a solid line) directly propagating to the fine particles P without scattering is condensed to the divided optical receiver 23 together with the scattered light (represented by a dotted line) using the condensing lens 22. It is noted that the condensing spot of the irradiated light condensed to the light-receiving surface of the divided optical receiver 23 is denoted by the reference symbol B in FIG. 3. Since the irradiated light has a numerical aperture (NA) smaller than that of the scattered light, the irradiated light condensing spot B on the light-receiving surface of the divided optical receiver 23 becomes larger than the scattered light condensing spot A.

In addition, the fluorescent or the scattered light generated, by the irradiated light condensed to the sample flow S, from the fine particles P or the fluorescent substance labeled onto the fine particles P is detected by the optical detector system (not shown) for measuring optical properties of the fine particles P. The optical detector system may include an object lens, a filter, a mirror, an optical detector, and the like and may have the same configuration as that of the fine particle measurement apparatus of the related art. The electric signal from the optical detector is supplied to measure the optical properties of the fine particles P. Similar to the fine particle measurement apparatus of the related art, as the parameters used to measure the optical properties, for example, the front scattered light is employed to determine the size of the fine particles P, the side scattered light is employed to determine the structure, and the fluorescent light is employed to determine whether the fluorescent substance labeled onto the fine particles P exists. In addition, the divided optical receiver 23 may be used in the optical detector for detecting the front scattered light of the fine particles P.

(2) Divided Optical Receiver

A configuration of the divided optical receiver 23 will be described with reference to FIG. 3. The divided optical receiver 23 is divided into a plurality of areas on the light-receiving surface where the scattered-light condensing spot A and the irradiated-light condensing spot B are condensed. Specifically, the divided optical receiver 23 is equally divided into a plurality of areas by boundary lines intersecting at the center of the light-receiving surface. More specifically, the divided optical receiver 23 includes four regions 231, 232, 233, and 234 equally divided by the two boundary lines intersecting at the center of the light-receiving surface.

As described above, in this optical system, the irradiated light uses the laser spot on the sample flow as an object point and uses the condensing spot on the light-receiving surface of the divided optical receiver as an image point. In addition, the scattered light uses the fine particles within the sample flow as an object point and uses the condensing spot on the light-receiving surface of the divided optical receiver as an image point. When positions of both object points of the irradiated light and the scattered light match with each other, positions of both image points of the irradiated light and the scattered light also match with each other. That is, when the position of the laser spot on the sample flow as an object point of the irradiated light matches with the position of the fine particle within the sample flow as an object point of the scattered light, the center points of the scattered-light condensing spot A and the irradiated-light condensing spot B corresponding to the image points of the scattered light and the irradiated light also match with each other as shown in FIG. 3.

Figure 4:
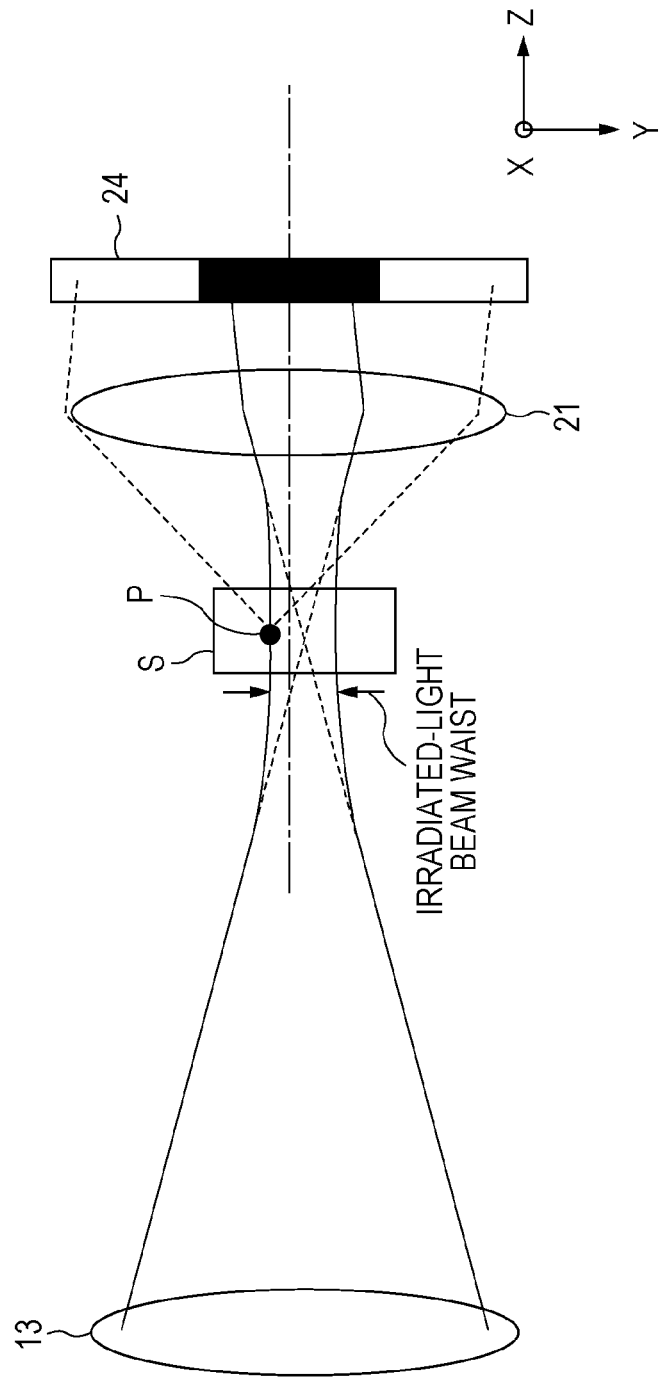
FIG. 4 is a schematic diagram illustrating a laser spot on the sample flow as an object point of the irradiated light and a flow-sending position of the fine particles within the sample flow as an object point of the scattered light.

FIG. 4 illustrates a laser spot on the sample flow S and a flow-sending position of the fine particles P within the sample flow S when the positions of both object points of the irradiated light and the scattered light do not match with each other. In FIG. 4, the solid line represents the irradiated light irradiated to the sample flow S and directly propagated without scattering, and the dotted line represents the scattered light scattered by the fine particles P. In FIG. 4, a distance between the two arrows represents a beam waist (spot diameter) of the laser spot condensed to the sample flow S. In addition, in FIG. 4, the flow-sending direction of the sample flow S is defined as the X-axis direction, the irradiation direction of the laser to the sample flow S is defined as the Z-axis direction, and the direction perpendicular to the ZX-plane is defined as the Y-axis direction.

The scattered light is generated from the fine particles P when the fine particles P is included in the beam waist of the laser spot condensed to the sample flow S. For this reason, the flow-sending position of the fine particle within the sample flow as an object point of the scattered light does not necessarily match with the position of the laser spot on the sample flow as an object point of the irradiated light. In FIG. 4, a state that the fine particles P flowing through the sample flow S passes through the edge of the beam waist of the laser spot is illustrated. Under the state shown in FIG. 4, the flow-sending position of the fine particle within the sample flow as an object point of the scattered light is deviated in the widthwise direction (Y-axis direction in FIG. 4) of the sample flow S with respect to the position of the laser spot on the sample flow as an object point of the irradiated light.

Figure 5:
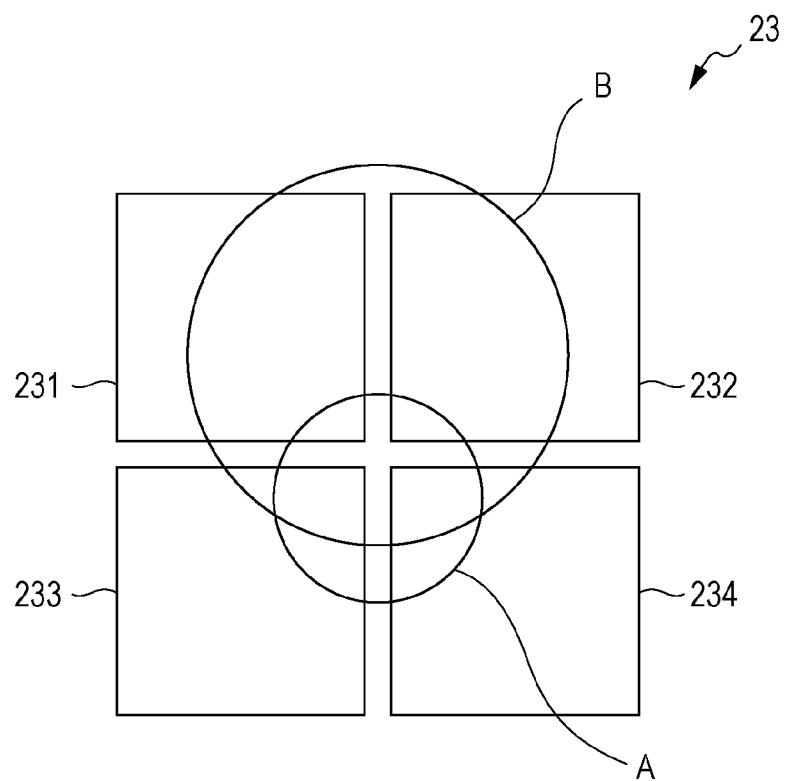
FIG. 5 is a schematic diagram illustrating positions of the irradiated-light condensing spot and the scattered-light condensing spot condensed on the light-receiving surface of the optical receiver when the laser spot on the sample flow does not match with the flow-sending position of the fine particles within the sample flow.

In this manner, when the positions of both object points do not match between the irradiated light and the scattered light, a deviation is also generated between the positions of the image point of the irradiated light and the image point of the scattered light. That is, when the position of the laser spot on the sample flow as an object point of the irradiated light does not match with the position of the fine particle within the sample flow as an object point of the scattered light, a deviation is also generated between the center positions of the scattered-light condensing spot A and the irradiated-light condensing spot B as the image points of the irradiated light and the scattered light as shown in FIG. 5.

(3) Control Unit

The fine particle measurement apparatus according to an embodiment of the disclosure detects the positions of the scattered-light condensing spot A and the irradiated-light condensing spot B based on the intensity of the signal (a position signal) obtained from the divided optical receiver 23. In addition, an optical axis calibration function is provided to match both the object points of the position of the laser spot on the sample flow and the position of the fine particle within the sample flow by correcting a deviation in the positions of both the image points and carrying out calibration to match both the positions.

The positions of the scattered-light condensing spot A and the irradiated-light condensing spot B can be detected using the signal intensity obtained from four regions 231, 232, 233, and 234 of the divided optical receiver 23. For example, as shown in FIG. 3, when the center of the light-receiving surface matches with the center position of the scattered-light condensing spot A or the irradiated-light condensing spot B, it is possible to obtain the same signal intensity from each region. Meanwhile, for example, as shown in FIG. 5, the center position of the scattered light condensing spot A or the irradiated light condensing spot B is deviated from the center of the light-receiving surface in the upper direction in the drawings, the signal intensity obtained from the regions 231 and 232 becomes larger than the signal intensity obtained from the regions 233 and 234. In addition, for example, when the center position of the scattered light condensing spot A or the irradiated light condensing spot B is deviated from the center of the light-receiving surface in the left direction in the drawings, the signal intensity obtained from the regions 231 and 233 becomes larger than the signal intensity obtained from the regions 232 and 234. Therefore, it is possible to detect the positions of the scattered light condensing spot A and the irradiated light condensing spot B based on a difference signal between a sum signal of the regions 231 and 232 and a sum signal of the regions 233 and 234 or a difference signal between a sum signal of the regions 231 and 233 and a sum signal of the regions 232 and 234.

The deviation of the position between the scattered-light condensing spot A and the irradiated-light condensing spot B can be corrected by adjusting the relative positions of the members such as the light source 11, the collimator lens 12, the condensing lens 13, and the flow path where the sample flow S is sent, included in the optical path. The positions of the members can be adjusted, for example, using a position controller 92 such as a feed screw, a guide, and a motor (see also, FIG. 1).

The fine particle measurement apparatus according to an embodiment of the disclosure includes a control unit 90 that controls the position controller 92 (see also, FIG. 1). The control unit 90 receives the signals output from each region of the divided optical receiver 23 and detects the positions of the scattered-light condensing spot A and the irradiated-light condensing spot B based on the intensities of the signals. In addition, the control unit drives the position controller such as a feed screw, a guide, and a motor to adjust the relative positions of each member included in the optical path such that the positions of the scattered-light condensing spot A and the irradiated-light condensing spot B match with each other.

As described above, in the fine particle measurement apparatus according to an embodiment of the disclosure, the optical axis calibration is carried out such that the positions of the irradiate-light condensing spot and the scattered-light condensing spot on the light-receiving surface of the optical receiver, as the image points of the irradiated light and the scattered light, match with each other. Therefore, it is possible to match the position of the laser spot on the sample flow as an object point of the irradiated light with the position of the fine particle within the sample flow as an object point of the scattered light. Therefore, even when a deviation is generated in the optical axis due to vibration during measurement or change in a pressure or a temperature, it is possible to automatically correct the deviation and carry out measurement with high precision.

In the present embodiment, description has been made to an example in which the mask 24 is interposed on the optical path between the sample flow S and the divided optical receiver 23 or arranged to be evacuated, and the position of the condensing spot of the scattered light and the position of the condensing spot of the irradiated light are separately detected. Typically, since the intensity of the irradiated light is larger than the intensity of the scattered light, it is preferable that a configuration including such a mask 24 is employed, and the position of the condensing spot of the scattered light is detected by excluding a leakage of the irradiation light. However, the positions of the condensing spots of the scattered light and the irradiated light may be simultaneously detected. As described in conjunction with FIG. 3, since the irradiated light has a smaller numerical aperture NA than that of the scattered light, the irradiated-light condensing spot B on the light-receiving surface of the divided optical receiver 23 becomes larger than the condensing spot A of the scattered light. In this regard, if the divided optical receiver 23 is divided into multiple portions including a portion corresponding to the scattered-light condensing spot A and a portion corresponding to the irradiated light condensing spot B using the difference between the sizes of these spots, it is possible to simultaneously detect the positions of both the condensing spots.

Although the divided optical receiver 23 includes four regions 231, 232, 233, and 234 in the present embodiment, the number of divided regions of the divided optical receiver 23 may be set to 2, 3, 5, or larger as long as the positions of the scattered-light condensing spot and the irradiated-light condensing spot can be detected based on the difference signal between the sum signals or the signals from one, two, or more regions. In addition, each region is not necessarily equally divided or is not necessarily divided by the boundary lines intersecting at the center of the light-receiving surface as long as the positions of the spots can be detected as described above.

2. Fine Particle Measurement Apparatus According to Second Embodiment

Figure 6:
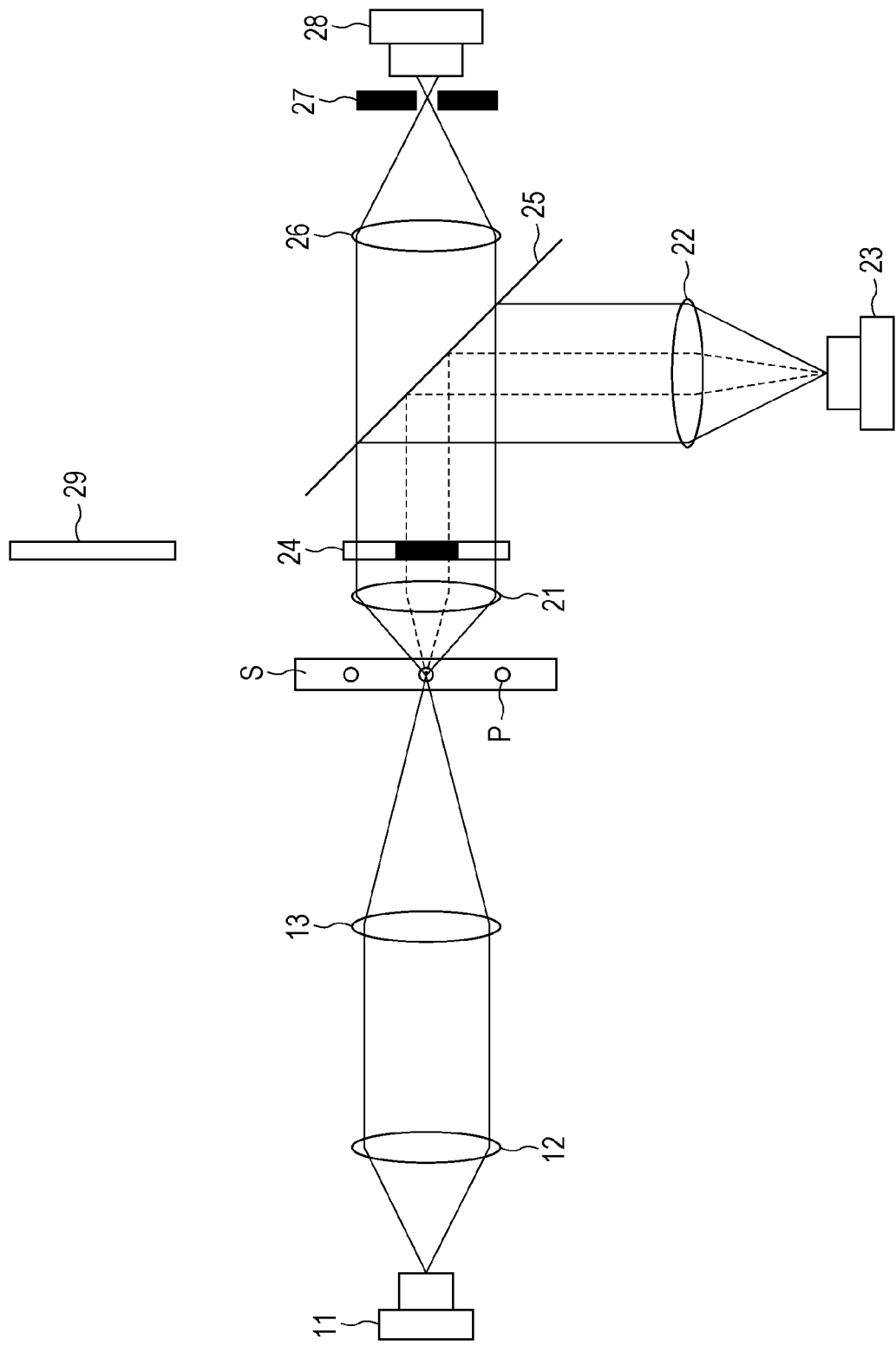
FIG. 6 is a schematic diagram illustrating a configuration of an optical path to detect a position of the scattered-light condensing spot position in the fine particle measurement apparatus according to a second embodiment of the disclosure.
Figure 7:
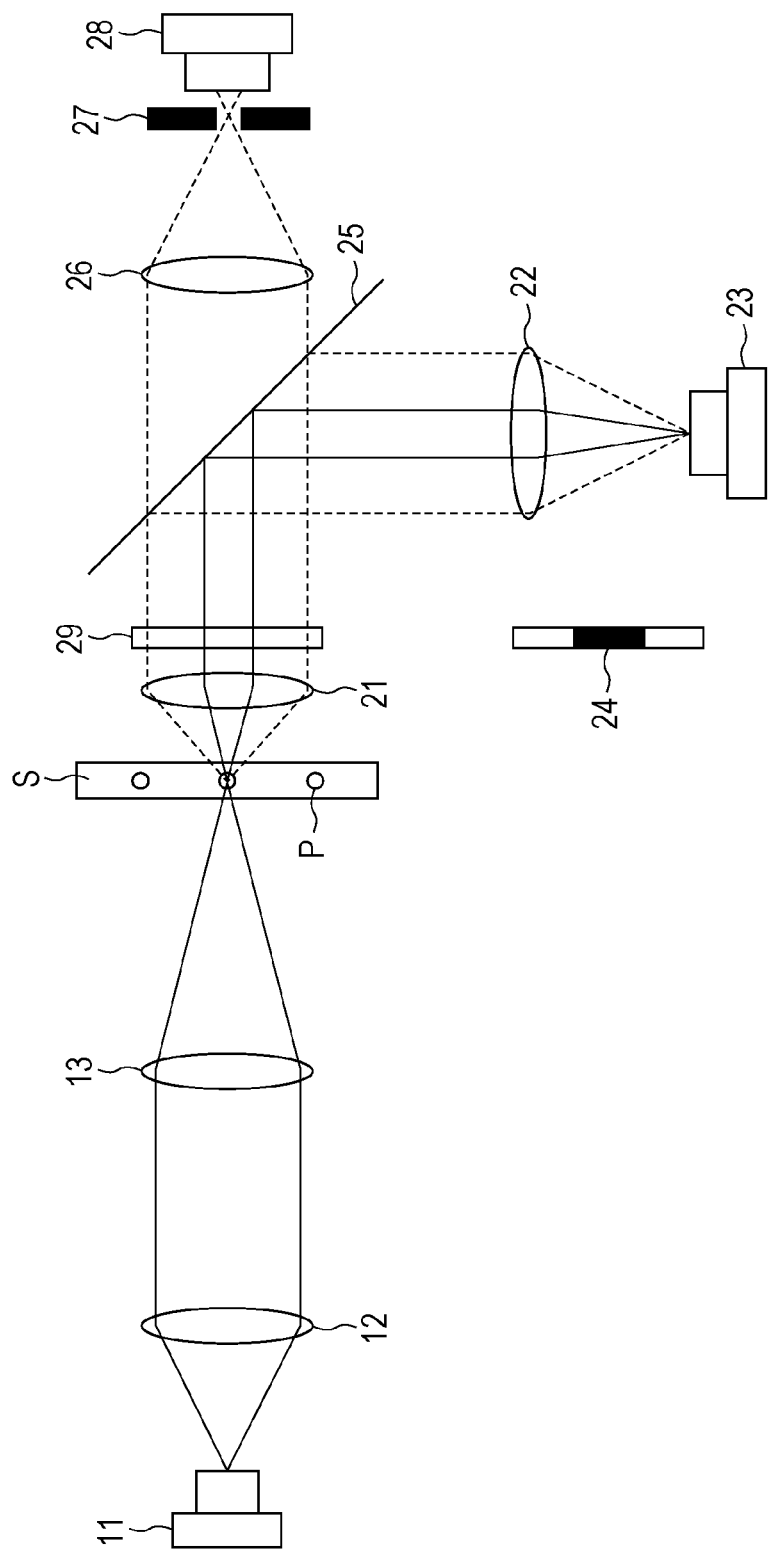
FIG. 7 is a schematic diagram illustrating a configuration of the optical path to detect a position of the irradiated-light condensing spot in the fine particle measurement apparatus according to a second embodiment of the disclosure.
Figure 8:
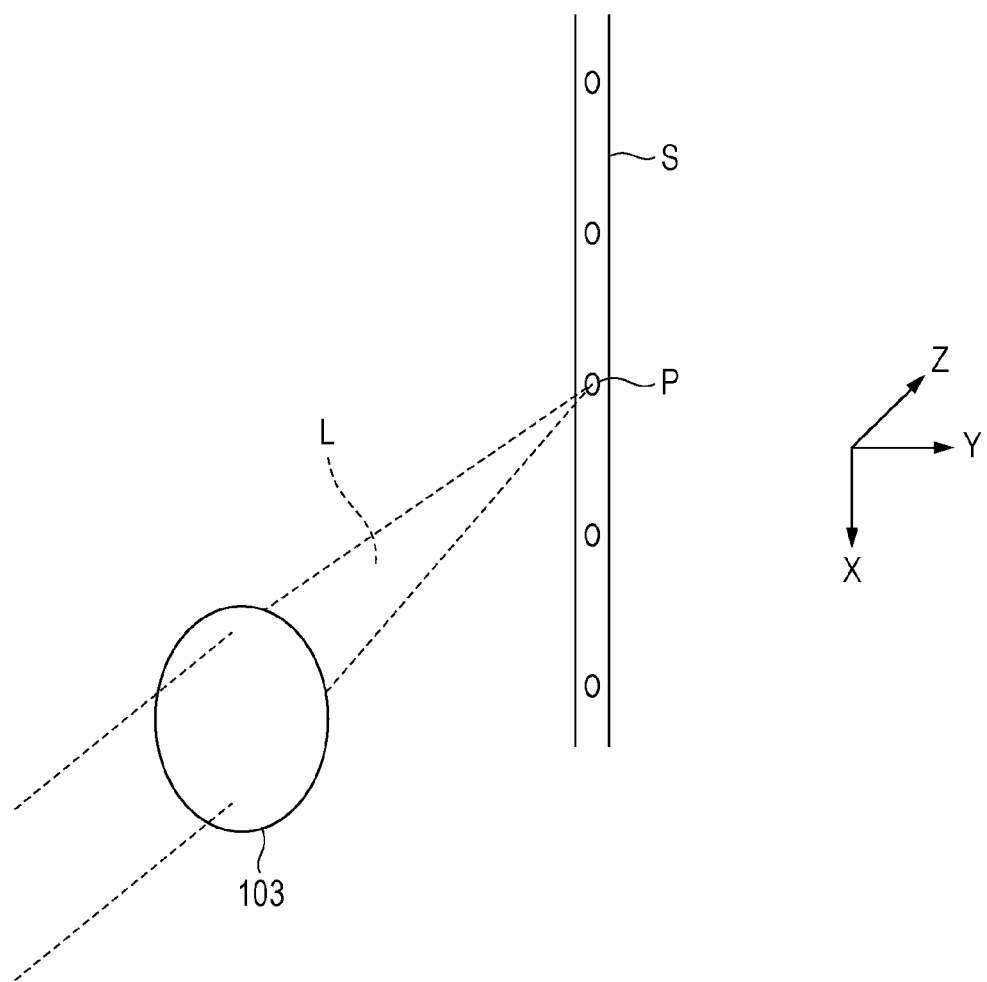
FIG. 8 is a schematic diagram illustrating a configuration of an optical irradiation system in the fine particle measurement apparatus of the related art.
Figure 9:
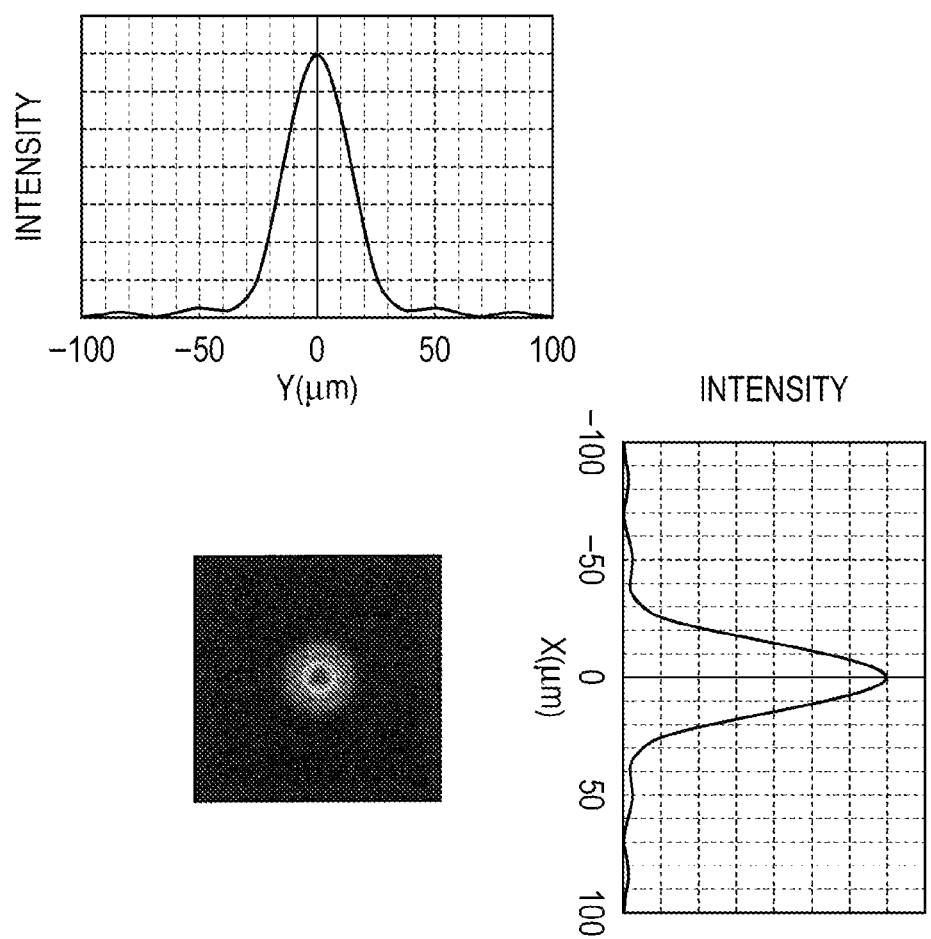
FIG. 9 is a diagram illustrating an intensity distribution of the laser spot in the fine particle measurement apparatus of the related art.

FIGS. 6 and 7 are schematic diagrams illustrating a configuration of the optical path of the fine particle measurement apparatus according to a second embodiment of the disclosure. FIG. 6 illustrates a configuration of the optical path when the position of the condensing spot of the scattered light is detected, and FIG. 7 illustrates a configuration of the optical path when the position of the condensing spot of the irradiated light is detected. The fine particle measurement apparatus according to the present embodiment is different from the aforementioned one of the first embodiment in that a pinhole for blocking stray light is disposed in the optical detector system for measuring the optical properties of the fine particles P.

The scattered light or the fluorescent light generated from the fine particles or the fluorescent substance labeled onto the fine particles by the irradiated light condensed to the sample flow is detected by the optical detector system, converted into the electric signal, and supplied for measurement of the optical properties of the fine particles. In this case, if self-fluorescent light generated from the microchip to which the sample flow is sent or stray light such as unnecessary scattered light is incident to the optical detector system, a measurement error may occur. Such stray light can be blocked by disposing a pinhole for blocking the stray light in the optical detector system. Hereinafter, a configuration of the optical path of the fine particle measurement apparatus according to the present embodiment will be described in detail.

In the drawings, the irradiated light (laser) emitted from the light source denoted by the reference numeral 11 is coupled to the substantially parallel light using the collimator lens 12 and condensed to the sample flow S, where the fine particles P pass through, using the condensing lens 13. The sample flow S may be sent to the inner side of the flow cell or the inner side of the flow path formed on the microchip.

The irradiated light irradiated to the sample flow S and directly propagated without scattering, and the scattered light scattered by the fine particles P are coupled to the substantially parallel light using the object lens 21 and guided to the polarization beam splitter 25. The polarization beam splitter 25 is an optical filter that splits a part of the scattered light based on a difference in the polarization direction. The scattered light irradiated to the sample flow S and scattered by the fine particles P is rotated in the polarization direction with respect to the irradiated light. For this reason, it is possible to split only the polarization component of the scattered light having a polarization direction perpendicular to the irradiated light from a mixture of the irradiated light and the scattered light by splitting the polarization component based on a difference in the polarization direction using the polarization beam splitter 25.

The scattered light component split by the polarization beam splitter 25 is condensed to the divided optical receiver 23 using the condense lens 22. The scattered light component condensed to the divided optical receiver 23 forms a condensing spot on the light-receiving surface thereof.

In the drawings, the reference numeral 24 denotes a mask including a blocking area for blocking the irradiated light and a transmitting area arranged around the blocking area to transmit the scattered light. The mask 24 is interposed on the optical path between the sample flow S and the divided optical receiver 23 or arranged to be evacuated.

As shown in FIG. 6, the irradiated light (represented by a dotted line) directly propagating onto the fine particle P without scattering when the mask 24 is interposed on the optical path between the sample flow S and the divided optical receiver 23 is blocked by the blocking area arranged in the center of the mask 24. Therefore, from the scattered light scattered by the fine particles P, only the polarization component of the scattered light having a polarization direction perpendicular to the irradiated light is condensed to the divided optical receiver 23 using the polarization beam splitter 25. In this case, the condensing spot of the scattered light condensed to the light-receiving surface of the divided optical receiver 23 is denoted by the reference numeral A in FIG. 3. In addition, since the configuration of the divided optical receiver 23 is similar to that described in conjunction with the first embodiment, description thereof will not be repeated here.

Meanwhile, in the scattered light scattered by the fine particles P, the polarization component of the scattered light having the same polarization direction as that of the irradiated light is condensed using the condensing lens 26 and detected by the optical receiver 28 for measurement of the optical properties of the fine particles P. In addition, the fluorescent light generated from the fine particles P or the fluorescent substance labeled onto the fine particles P by the irradiated light condensed to the sample flow S is detected by an optical detector system (not shown). In this case, it is possible to prevent self-fluorescent light generated from the microchip or stray light such as unnecessary scattered light from being incident to the optical receiver 28 by arranging the pinhole 27.

According to the present embodiment, the polarization component of the scattered light having a polarization direction perpendicular to the irradiated light is split into the divided optical receiver 23 using the polarization beam splitter 25. For this reason, the irradiated light irradiated to the sample flow S and directly propagated without scattering is not split into the divided optical receiver 23 without change. In this regard, according to the present embodiment, an optical filter 29 for rotating the polarization direction of the irradiation light is interposed on the optical path between the polarization beam splitter 25 and the sample flow S or arranged to be evacuated. As the optical filter 29, for example, a half wavelength plate is preferably used. Hereinafter, the optical filter 29 is called a "half wavelength plate 29." The half wavelength plate 29 is preferably arranged replaceable with the mask 24.

As shown in FIG. 7, when the half wavelength plate 29 is interposed on the optical path between the sample flow S and the polarization beam splitter 25, the irradiated light (represented by the solid line in the drawing) which directly propagates without scattering by the fine particles P has a polarization direction rotated by the half wavelength plate 29 and is guided to the divided optical receiver 23 using the polarization beam splitter 25. The irradiated light guided to the divided optical receiver 23 is condensed to the light-receiving surface of the divided optical receiver 23 using the condensing lens 22 to form the condensing spot. In this case, the condensing spot of the irradiated light condensed to the light-receiver surface of the divided optical receiver 23 is represented by a reference symbol B in FIG. 3.

Even in this optical system, the irradiated light uses the laser spot on the sample flow as an object point and uses the condensing spot on the light-receiving surface of the divided optical receiver as an image spot. In addition, the scattered light uses the fine particle within the sample flow as an object point and uses the condensing spot on the light-receiver surface of the divided optical receiver as an image point. When the positions of both object points of the irradiated light and the scattered light match with each other, the image point of the irradiated light and the image point of the scattered light match with each other.

Figure 3:
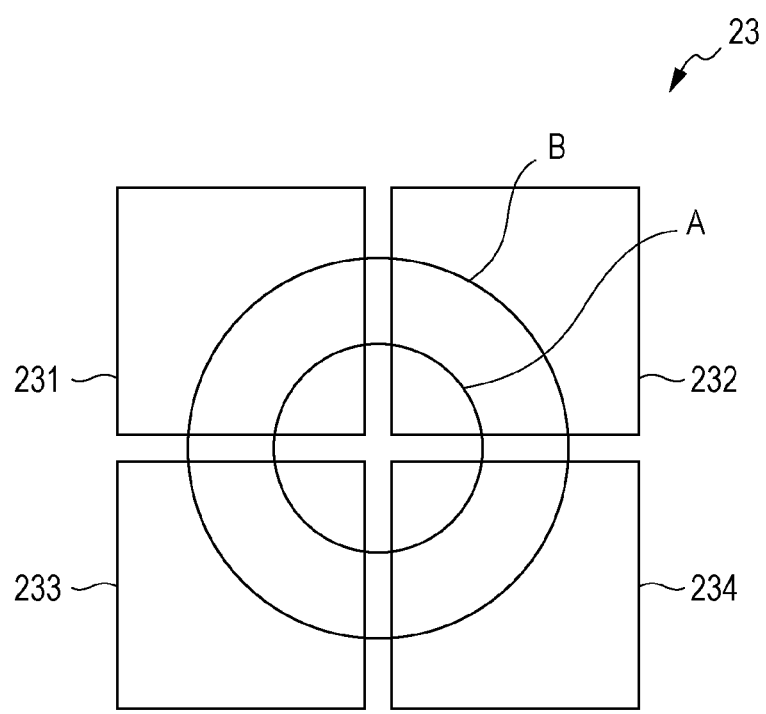
FIG. 3 is a schematic diagram illustrating a configuration of the light-receiving surface of the divided optical receiver and positions of the irradiated-light condensing spot and the scattered-light condensing spot on a light-receiving surface of the optical receiver as an image point of the irradiated light and the scattered light.

That is, when the position of the laser spot on the sample flow as an object point of the irradiated light matches with the position of the fine particle within the sample flow as an object point of the scattered light, the center positions of the scattered-light condensing spot A and the irradiated-light condensing spot B as image points of the irradiated light and the scattered light also match with each other as shown in FIG. 3. In contrast, when the position of the laser spot on the sample flow as an object point of the irradiated light does not match with the position of the fine particle within the sample flow as an object point of the scattered light, the center positions of the scattered-light condensing spot A and the irradiated-light condensing spot B as the image points of the irradiated light and the scattered light are deviated as shown in FIG. 5.

The fine particle measurement apparatus according to the present disclosure detects the positions of the scattered-light condensing spot A and the irradiated-light condensing spot B based on the intensities of the signal (position signal) obtained from the divided optical receiver 23. In addition, an optical axis calibration function is provided to match both the object points between the position of the laser spot on the sample flow and the position of the fine particle within the sample flow by correcting a deviation in the positions of both the image points to match with each other.

The detection of the positions of the scattered light condensing spot A and the irradiated light condensing spot B or the correction of a deviation in the detected positions of the scattered-light condensing spot A and the irradiated-light condensing spot B may be carried out as in the fine particle measurement apparatus according to the first embodiment.

As described above, in the fine particle measurement apparatus according to the present disclosure, by carrying out the optical axis calibration such that the positions of the irradiated-light condensing spot and the scattered-light condensing spot on the light-receiving surface of the optical receiver as the image points of the irradiated light and the scattered light match with each other, it is possible to match the position of the laser spot on the sample flow as an object point of the irradiated light with the position of the fine particle within the sample flow as an object point of the scattered light. Therefore, even when a deviation is generated in the optical axis due to vibration or change in the temperature or pressure during measurement, it is possible to automatically correct the deviation and carry out measurement with high precision.

According to the present embodiment, in the scattered light scattered by the fine particle, a polarization component of the scattered light having a polarization direction perpendicular to the irradiated light is condensed to the divided optical receiver 23 for detecting the position of the condensing spot of the scattered light, and the polarization component of the scattered light having the same polarization direction as that of the irradiated light is condensed to the optical receiver 28 for measuring the optical properties of the fine particles using the polarization beam splitter 25. The polarization component of the scattered light having a polarization direction perpendicular to that of the irradiated light has a smaller intensity than that of the polarization component of the scattered light having the same polarization direction as that of the irradiated light. For this reason, in a case where the signal intensity of the optical receiver 28 has a priority to measure the optical properties of the fine particles with high sensitivity, the aforementioned configuration is very preferable. Meanwhile, in a case where the position of the condensing spot of the scattered light is measured with higher sensitivity, the splitting of the scattered light using the polarization beam splitter 25 may be made such that the polarization component of the scattered light having the same polarization direction as that of the irradiated light is condensed to the divided optical receiver 23, and the polarization component of the scattered light having a polarization direction perpendicular to the irradiated light is condensed to the optical receiver 28.

According to the present embodiment, similar to the first embodiment, the position of the condensing spot of the scattered light and the position of the condensing spot of the irradiated light may be simultaneously detected. In addition, the number of divided regions of the divided optical receiver 23 may be set to 2, 3, 5, or higher, and the divided optical receiver 23 is not necessarily equally divided. Furthermore, the divided optical receiver 23 is not necessarily divided by the boundary lines intersecting at the center of the light-receiving surface.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An optical axis calibration method in a fine particle measurement apparatus, the method comprising:
    condensing irradiated light irradiated to a sample flow where fine particles pass through and directly propagating the light without scattering, and scattered light scattered by the fine particles to an optical receiver divided into a plurality of regions;
    detecting positions of condensing spots of the irradiated light and the scattered light based on signal intensities of each region of the optical receiver; and
    calibrating relative positions of members of an optical path such that the positions of the condensing spots of the irradiated light and the scattered light match with each other, the control unit thereby being configured to automatically correct any detected optical axis deviations.

2. The optical axis calibration method according to claim 1, wherein the light condensing unit includes an optical filter having a blocking area for blocking the irradiated light and a transmitting area arranged around the blocking area to transmit the scattered light, the optical filter being configured to be moved between an optical path position that intersects an optical path extending between the sample flow and the optical receiver and an evacuated position that does not intersect said optical path.

* * * * *